United States Patent [19]

Smith et al.

[11] Patent Number: 5,143,725
[45] Date of Patent: Sep. 1, 1992

[54] METHOD AND COMPOSITION FOR ATTRACTING MULLEIN BUGS

[75] Inventors: Robert F. Smith, Kentville; Harold D. Pierce, Jr., Burnaby; John H. Borden, Burnaby; Leslie J. Chong, Burnaby; Nairn W. Hay, Vancouver, all of Canada

[73] Assignee: Phero Tech Inc., Delta, Canada

[21] Appl. No.: 620,279

[22] Filed: Nov. 30, 1990

[51] Int. Cl.⁵ .................... A61K 31/235; A01N 25/00
[52] U.S. Cl. ...................................... 424/84; 514/546
[58] Field of Search .......................... 514/546; 424/84

[56] References Cited

U.S. PATENT DOCUMENTS

| | | | |
|---|---|---|---|
| 3,018,219 | 1/1962 | Jacobson | 424/311 |
| 3,702,358 | 11/1972 | Green et al. | 424/84 |
| 4,410,509 | 10/1983 | Carrol | 424/84 |

OTHER PUBLICATIONS

Jeffrey R. Aldrich, *Chemical Ecology of the Heteroptera*, Annual Rev. Entomel, 1988, 33: 211–238.

G. Boivin and R. K. Stewart, *Attraction of Male Green Apple Bugs, Lygocoris communis (Hemiptera: Miridae), To Caged Females*, Department of Entomology, Macdonald Campus of McGill University, vol. 114 (1982); pp. 765–766.

Harold F. Madsen, *Monitoring Codling Moth Populations in British Columbia*, in E. Mitchell (ed.), Management of Insect Pests with Semiochemicals, Proceedings of International Colloquium, Held Mar. 23–28, 1980, Gainesville, FL., pp. 57–62.

R. D. McMullen and C. Jong, *The Biology and Influence of Pesticides on Campylomma verbasci (Heteroptera: Miridae)*, The Canadian Entomologist, vol. 102, Nov. 1970, pp. 1390–1394.

E. S. C. Smith, *Presence of a Sex Attractant Pheromone in Helopeltis clavifer (Walker) (Heteroptera: Miridae)*, Department of Primary Industry, Papua, New Guinea, 1977, 16: 113–116.

Brian W. Staddon, *The Scent Glands of Heteroptera*, Advances in Insect Physiology 1986, pp. 351–419.

H. M. A. Thistlewood, *The Bionomics and Monitoring of Campylomma verbasci (Meyer) on Apple in the Okanagan Valley*, British Columbia, Thesis, Simon Fraser University, Jan. 1986, pp. iii–iv and 24–33.

J. M. Hardman et al., *Pest Abundance, Pesticide Usage and Levels of Fruit Damage in a Pest Management Program in Nova Scotia Apple Orchards*, Talk No. 31, Section 20, Problems and Prospects of Integrated Plant Protection Against Major Arthropod Pests, Aug. 21, 1984, XVII International Congress of Entomology, Hamburg, Federal Republic of Germany.

M. E. Whalon et al., *Apple IPM Implementation in North America*, Annual Rev. Entomol. 1984, 29: 435–470.

H. D. Pierce, Jr. et al., *Methodology For Isolation and Analysis of Aggregation Pheromones in the Genera Cryptolestes and Oryzaephilus* (Coleoptera: Cucujidae), Department of Chemistry, Department of Biological Sciences, Simon Fraser University, Burnaby, B.C., Canada, 1984, pp. 121–137.

Guy Boivin et al., *Sticky Traps for Monitoring Phytophagous Mirids (Hemiptera: Miridae) in an Apple Orchard in Southwestern Quebec*, Entomological Society of America, 1982, pp. 1067–1070.

J. R. Aldrich et al., *Lygus Bug Pheromones vis-a-vis Stink Bugs*, Beltwide Cotton Production Research Conferences, 1988, pp. 213–216.

*Spray Guide for Tree Fruits in Eastern Washington*, Cooperative Extension, College of Agriculture & Home Economics, Washington State University 1988.

*Primary Examiner*—S. J. Friedman
*Attorney, Agent, or Firm*—Seed and Berry

[57] ABSTRACT

This invention relates to a novel composition for attracting mullein bugs, *Campylomma verbasci*, a pest of tree fruit orchards in North America. The invention also pertains to methods of attracting mullein bugs and predicting future population levels of these insects. The composition for attracting male mullein bugs, *Campylomma verbasci*, comprises a mixture of butyl butyrate and 2 (E)-crotyl butyrate.

6 Claims, 4 Drawing Sheets

TIME, min.

METHOD AND COMPOSITION FOR ATTRACTING MULLEIN BUGS

FIELD OF THE INVENTION

This invention relates to a novel composition for attracting mullein bugs, *Campylomma verbasci*, a pest of tree fruit orchards in North America. The invention also pertains to methods of attracting mullein bugs and predicting future propulation levels of these insects.

BACKGROUND OF THE INVENTION

The mullein bug, *Campylomma verbasci* (Heteroptera: Miridae), is an introduced insect, not native to North America. It has three or four generations per year (McMullen and Jong 1970). The summer months are spent on common mullein, *Verbascum thapsus*, its principal herbacious host. After two generations on this plant, adults migrate to woody host plants (usually apple or pear trees) to oviposit overwintering eggs in the bark (McMullen and Jong 1970). With approach of spring, emboyonic development accelerates. Typically, first generation eggs hatch during the "bloom" through "calyx" stages (Thistlewood 1986) of apple development. Neonate nymphs first feed on over-wintering mite eggs and then move to apples. Damage occurs when these nymphs puncture and feed on fruitlets, inducing the formation of corky tissue, dimples and pits and downgrading of the fruit to culls.

Management of *c. verbasci* is based on economic thresholds of injury levels that correlate density of nymphs in the spring with subsequent fruit damage (Whalon and Croft 1984, Thistlewood et al. 1989a). Sampling is done using a 40×40 cm tapping tray; nymphs are jarred from the branch by several sharp blows with a padded stick (Hardman et al. 1984, Washington State University 1988). Although this method generally leads to effective predictions (Thistlewood and McMullen 1989), the method is deficient in several ways. It is time consuming and requires many samples per hatch for reliable prediction. There is often little time between egg hatch and the moment at which injury to the fruit occurs. Adverse weather can prolong both egg hatch and the sampling routine. The limb-tap method assumes that the majority of overwintering eggs have hatched, while maximal hatching varies considerably from year to year (Thistlewood 1986). Finally, although only a few orchards in any given year may sustain damage, it is necessary to sample all orchards intensively because there is no means of predicting beforehand which ones are most likely to harbour populations above the economic threshold.

Pheromones have been used to monitor lepidopteran orchard pests such as the codling moth, *Cydia pomenella* (Madsen 1981). Thistlewood et al. (1989b) have shown that female mullein bugs emit a sex pheromone that attracts males to female-baited traps in a manner similar to that found in the other mirids: *Lyqus lineolaris* (P. de Beaurois) (Scales 1968), *Lygocoris communis* (Knight) (Boivin and Stewart 1982), *Distantiella theobroma* (Dist.) (King 1973) and *Heloceltis clavifer* (Walker) (Smith 1977, Staddon 1986).

The exact identity of the pheromone for *C. verbasci*, or any mirid, had not previously been determined (Aldrich 1988). It was not possible to predict or infer the identity of the *C. verbasci* sex pheromone, nor was it possible to predict or infer the response of insects in nature to it, or to predict or infer that it could be used as a predictive tool in orchard pest management.

SUMMARY OF THE INVENTION

A composition for attracting male *Camoylomma verbasci* comprising butyl butyrate and 2(E)-crotyl butyrate, which are the natural components of the sex pheromone of *C. verbasci*.

In the composition, the butyl butyrate and the 2(E)-crotyl butyrate may be synthetic. The ratio by weight of butyl butyrate to 2(E)-crotyl butyrate may be 16 to 1.

In another aspect, the invention pertains to a method of attracting male *C. verbasci* which comprises the deployment of butyl butyrate and 2(E)-crotyl butyrate in sticky traps hung in or near tree fruit orchards. In a further aspect, the invention involves a method of predicting in the fall, the population levels of *C. verbasci* in the next spring. The method comprises the deployment of traps baited with female C. verbasci in orchards in the fall, and using the number of captured male *C. verbasci* to forecast the density of damaging nymph populations the following spring. In a further aspect, the invention is directed to a method of predicting populations of nymphs in the spring based on the numbers of *C. verbasci* males captured in the fall in traps baited with a mixture of synthetic butyl butyrate and 2(E-crotyl butyrate.

DETAILED DESCRIPTION OF SPECIFIC EMBODIMENTS OF THE INVENTION

We have discovered and demonstrated that the female-produced sex pheromone of the mullein bug, *Campylomma verbasci* is comprised of a 16:1 mixture of butyl butyrate and 2(E)-crotyl butyrate. The practical essence of our discovery is that a composition of natural or synthetic butyl butyrate and 2(E)-crotyl butyrate mimics the attraction to male C. Yerbasci emitted by female *C. verbasci*. This composition is as effective in traps in attracting and trapping male *C. verbasci* in the fall as virgin female *C. verbasci*. The numbers of captured males attracted to the novel composition can thus be used to predict the magnitude of nymph population in the spring.

EXAMPLE 1

This example describes the chemical isolation and identification, and confirmation by field bioassays, of the sex pheromone of *C. verbasci*, and its activity.

Butyl and hexyl butyrate, butyryl chloride, 2(E)-crotonaldehyde, and 1-hexanol were purchased. Hexyl acetate was prepared by reaction of 1-hexanol with acetic anhydride in pyridine. Reduction of 2(E)-crotonaldehyde with sodium borohydride in 50% aqueous ethanol gave a 2(E)-crotyl alcohol containing 4.3% 1-butanol and 1.7% Z isomer. 2(E)-crotyl butyrate was prepared by reaction of 2(E)-crotyl alcohol with butyryl chloride in ether in the presence of tiethylamine. After work-up and distillation at reduced pressure the ester was 90.6% pure and contained 4.5% butyl butyrate.

Hewlett-Packard 5830, 5880 and 5890 TM gas chromatographs equipped with capillary inlet systems and flame-ionization detectors were employed for analyses by gas-liquid partition chromatography (GC). Glass columns (30–40 m×0.5 mm ID) coated with SP1000 and fused with silica columns (15 m×0.25 mm ID) coated with DB-1 were used. The injection port and detector temperatures were 260° and 270° C. respectively. A Hewlett-Packard 5895B GC/MS/DS TM was employed for coupled gas chromatography-mass spectroscopy (GC-MS). Fused silica columns (0.32 mm ID) coated with DB-1 (30 or 60 m) or DB-WAX (60 m) were coupled directly into the ion source. The injection port, transfer line and ion source temperatures were 260°, 250° and 200° C. respectively. Helium was the carrier gas for GC and GC-MS.

Mullein bugs were mass collected from natural stands of *V. thapsus*. Females were crushed in double distilled pentane at −40° C., and the extracts were stored at −20° C. in screwcap vials with Teflon TM -lined lids. The strength of extracts was expressed as bug equivalents (b.eq.) (one crushed female bug or any undiluted fraction thereof =1 b.eq.). i Volatiles from live *C. verbasci* females were collected in Porapak Q TM (ethylvinyl benzene-divinyl benzene copolymer, 50–80 mesh, Applied Science Laboratories Inc.) using methods described by Pierce et al. (1984). Air was drawn at a rate of about 4 L per min. through a glass aeration chamber (15 cm O.D. by 30 cm) containing females on mullein stalks. The aeration chamber was cleaned and fresh plant material and female bugs were added at approximately 48 h intervals. Captured volatiles were expressed as bug-hours (b.h.) (one b.h. =volatiles produced by 1 female for 1 hour).

Volatiles from female bugs or mullein were recovered from Porapak Q TM by overnight extraction in a Soxhlet TM extractor with pentane. The solution was concentrated to approximately 10 mL by distilling off the pentane through a 30 cm Dufton TM column. A micro steam distillation-continuous extraction apparatus (Godefroot et al. 1985) was employed for the isolation of volatiles from the pentane extracts of crushed bugs.

Extracts were fractionated in a micropreparative gas chromatograph (Pierce et al. 1984). A stainless steel column (3.05 m×3.18 mm OD) packed with 10% SP1000 on Supelcoport (100/120) TM was used for fractionation of steam-distilled or Porapak Q-trapped female volatiles. Before separation, a portion of the solution containing the volatiles was set aside for field tests. The remainder of the sample was concentrated under a stream of nitrogen at −10° C. to approximately 30 µL before injection in the the chromatograph. Fractions were rinsed from the collection tubes into 1 mL volumetric tubes containing about 200 µL of hexane or pentane which were made up to volume with hexane. Aliquots from these were transferred to screw cap vials for later release in field traps.

Five bioassay experiments were conducted in the field at the Agriculture Canada Research Station, Summerland, British Columbia, Canada. This region is known as the Okanagan Valley. Unless stated otherwise, all treatments were replicated four times in a completely randomized design. A 2 L ice-cream carton trap with a sticky liner insert was used in all experiments, and set at a height of 1.5 m in both orchard and mullein field test sites. Those in an orchard were placed 0.5 m from the outer canopy edge. All bait receptacles were suspended inside the centre of the trap.

Data were transformed to $\sqrt{n+0.5}$, prior to statistical analysis, to meet the assumptions for analysis of variance, prior to Tukey's pairwise comparison of the means (SAS Institute 1985).

In Experiment 1, fractions of crushed bug extracts (250 b.eq.) or unfractionated extract (100 b.eq.) were dissolved in 2 mL of pentane and held in a 5 mL glass vial. The screw cap for each vial was drilled to give a 2 mm vent. Traps were deployed in a mixed planting of "Red Delicious" and "Golden Delicious" apple trees for four days commencing Aug. 29, 1986. Treatments were separated by at least 6 m, and replicates by 8 m.

Porapak Q-collected pheromone or fractions thereof were field-tested in Experiment 2 to establish a dose-response relationship. Concentrated extract in a diethyl ether/pentane solvent was transferred by syringe into a 2 mL centrifuge tube and the cap sealed. Treatments were extracts at 29,400, 9,800 and 2,900 b.h., solvent control (ether/pentane), and a caged-female control (five per trap). The caged females were replicated three times; all other treatments had four replicates. This experiment was conducted over a 6 day period commencing Sep. 6, 1987.

In Experiment 3, Porapak Q extract fractions were syringed into a 2 mL centrifuge tube through a 2 mm diameter hole in the cap. Fractions were tested at a strength of 8,000 b.h. Control stimuli were five caged females and solvent. The tests ran for 11 days commencing Sep. 21, 1987. The objective was to verify the activity zone, initially defined by the fractions from the crude insect crushes. In particular, since the Porapak Q method was now the sole means of lure collection, confirmation of previous results served to double check this procedure's accuracy. This experiment was set in an apple orchard; live-caged females had three replicates, all others had four.

A fourth experiment using 10,000 b.h. was undertaken in the same orchard to resolve whether butyl butyrate alone had any attractiveness.

The fifth and final experiment involving 7,000 b.h. was conducted to determine the identity of the minor component that interacts in combination with butyl butyrate. It was set up in a mullein field setting in a 2×2 m grid in August 1988. There were 4 m between treatments and 8 m between replicates.

Pheromone activity was centred in fraction #2 of the bug distillate extract including butyl butyrate and minor compounds eluting after it and before hexyl butyrate (Table 1, Experiment 1). We noted that the total extract, despite being 1.5 times less concentrated than fraction #2, trapped significant numbers of males.

We also found that Porapak Q-captured female volatiles were as active at 29,400 b.h. as five females (Table 1, Experiment 2). Attraction was less at 9,800 or 2,900 b.h., but still higher than the solvent control at the latter dosage. The capture rates in comparison to that of live females may be misleading because the longevity of the extracts was <4 days and attraction must have declined rapidly once they were placed in the traps.

We found that the Porapak Q extract and a combination of fractions #1 and #2 (FIG. 1B) achieved captures approaching those of caged females (Table 1, Experiment 3,4), verifying the response to fraction #2 of the female extract (Table 1, Experiment 1). Hexyl butyrate (fraction #3) did not influence male captures in combination with other fractions (Table 1, Experiments 1, 3) and was eliminated as a candidate pheromone. Butyl butyrate alone (FIG. 1B, fraction #1) was inactive (Table 1, Experiment 1) yet attraction was achieved when it was combined with the minor compounds in fraction #2, which in turn were inert when tested alone (Table 1, Experiment 3). Further research then focused on these minor compounds.

Figure 1A:
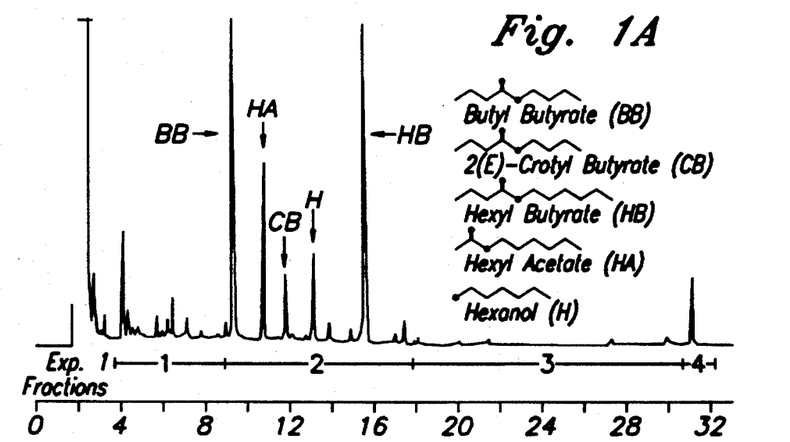
FIG. 1 depicts a gas chromatogram of *C. verbasci* volatiles. A) volatiles from steam distillate of females. B) Porapak Q-trapped volatiles from females feeding on mullein. C) volatiles from steam distillate of males. BB - butyl butyrate, HA - hexyl acetate, CB - 2-(E) -crotyl butyrate, H =1 hexanol, HB =hexyl butyrate, and 0 - 1-octen-3 ol (from mold growing on mullein).
Figure 1B:
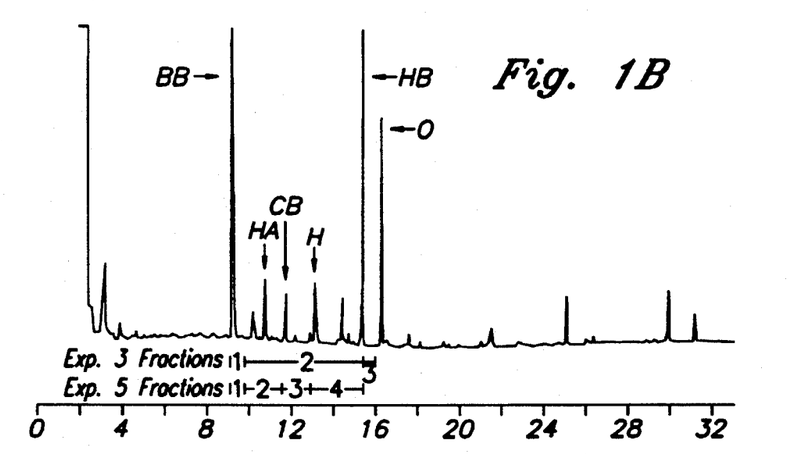
Figure 1C:
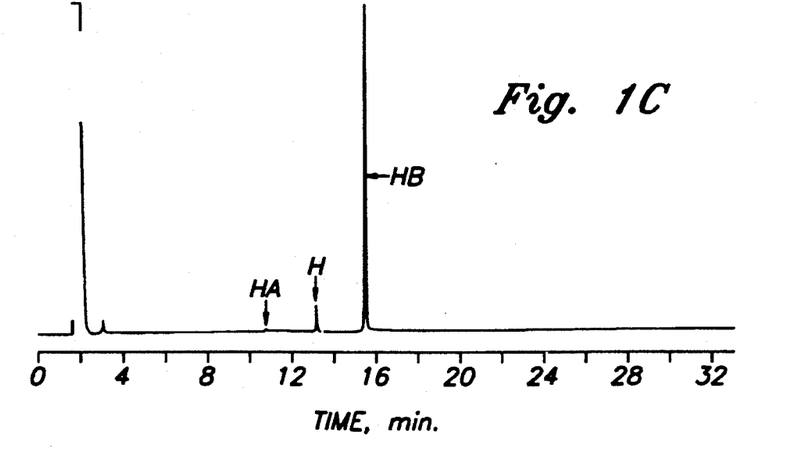

The mass spectrum of peak CB (FIG. 1A, B) exhibited a base peak at m/z $89(C_4H_{11}O_2^{30})$, the base peak in the spectrum of butyl butyrate (MW - 144). Since females of several Lvous spp. contain and emit hexyl and 2(E)-hexenyl butyrate (Aldrich et al. 1988), peak CB was hypothesized to be an unsaturated companion to butyl butyrate, i.e. 2(E)-crotyl butyrate. Comparison of the mass spectrum and retention time of the unknown to those of the synthetic sample confirmed this hypothesis.

Present in both male and female volatiles were hexyl acetate and 1- hexanol. These compounds were identified by GC-MS and a search of reference spectra. The assignments were confirmed by comparison of their mass spectra and retention times to authentic samples.

TABLE 1

Captures of male *C. verbasci* in traps baited with fractions of crushed female extract or the extract of Porapak Q-Captured female volatiles, 1986–1988

| Exp. no. and Description | Treatments[a] | Stimulus Strength | No. of Replicates | Mean no. Males Captured ± S.E.[b] |
|---|---|---|---|---|
| 1 Crushed bug fractions | Female extract | 100 b.eq. | 3 | 17.3 ± 1.8b |
| | Fraction #1 | 250 b.eq. | 4 | 0.3 ± 0.3d |
| | Fraction #2 | 250 b.eq. | 4 | 35.8 ± 5.4a |
| | Fraction #3 | 250 b.eq. | 4 | 0.5 ± 0.3cd |
| | Fraction #4 | 250 b.eq. | 3 | 2.0 ± 0.6c |
| | Pentane | 5 mL | 4 | 0.0 ± 0.0d |
| 2 Dose-response Porapak Q collected volatiles | 5 live females | | 3 | 8.3a |
| | Captured volatiles | 29,000 b.h. | 4 | 5.8ab |
| | Captured volatiles | 9,800 b.h. | 4 | 3.3bc |
| | Captured volatiles | 2,900 b.h. | 4 | 2.0c |
| | Pentane | 5 mL | 4 | 0.0d |
| 3 Porapak Q extract fractions | 5 live-caged females | | 4 | 17.0 ± 3.8a |
| | Porapak Q extract | 8,000 b.h. | 4 | 8.3 ± 0.6b |
| | Fraction #'s 1 and 2 | 8,000 b.h. | 4 | 11.5 ± 3.6ab |
| | Fraction #2 | 8,000 b.h. | 4 | 0.5 ± 0.5c |
| | Fraction #'s 2 and 3 | 8,000 b.h. | 4 | 0.0 ± 0.0c |
| 4 Porapak Q test of | 5 live-caged females | | 3 | 7.7 ± 1.2a |
| | Porapak Q | 10,000 b.h. | 4 | 12.1 ± 1.1a |
| Fraction 1 (butyl butyrate) alone | extract Fraction E's 1 and 2 from Exp. 3 | 10,000 b.h. | 4 | 9.8 ± 2.9a |
| 5 Porapak Q extract, identity of minor component | 5 live-caged females | | 4 | 5.0 ± 0.6a |
| | Porapak Q extract | 7,000 b.h. | 4 | 4.0 ± 0.4ab |
| | Fraction #1 + crotyl butryate | 7,000 b.h. | 4 | 3.3 ± 0.6b |
| | Fraction #1 + hexyl acetate | 7,000 b.h. | 4 | 1.0 ± 0.5c |
| | Hexane | 5 mL | 4 | 1.1 ± 0.5c |

[a]Fraction numbers correspond to those on GLC traces of female extracts or extracts of Porapak Q-captured female volatiles.
[b]Means followed by a common letter are not significantly different, P < 0.05, Tukey's Pairwise Comparison test, SAS Institute 1985.

GC-MS revealed crotyl butyrate and hexyl acetate as two of the trace chemicals in fraction #2. Recombining crotyl butyrate, but not hexyl acetate, with butyl butyrate gave capture rates equalling that of the complete extract and approaching that of the five live-caged females (Table 1, Experiment 5).

EXAMPLE 2

This example describes two experiments that were conducted with synthetic pheromone. The objectives were to verify that the synthetic pheromone determined in Example 1 mimicked the attractiveness of female *C. verbasci* and to determine effective release rates for the synthetic in the field.

Synthetic n-butyl butyrate and 2(E)-crotyl butyrate (16:1, weight:weight) were tested in a three-replicate dosage response experiment conducted in a "Bartlett" pear tree orchard, in September 1988. Persistence of the lure was enhanced by mixing the butyrates with light paraffin oil. Treatments were 4 mL oil in a 6 mL glass vial containing a mixture of butyl and crotyl butyrate at 2.0, 1.0, 0.1 and 0.01%, compared with paraffin oil and caged-female controls. Numbers of males captured were transformed to (n +1) prior to statistical analysis and pairwise comparison of the means using the Least Significant Difference test (SAS Institute 1985).

Synthetic butyl butyrate and crotyl butyrate (16:1 weight:weight) were also tested as candidate pheromones in three release devices and compared as baits to five live caged females. Dispensers were: 1) coagulation tubes 0.98±0.03 mm I.D.×40 mm, 2) capillary tubes 1.21 ±0.03 mm I.D.×40 mm, and 3) 20 mL glass vials. Four μL of the butyrate mixture was transferred by syringe into the tubes, while 4 vL of the 16:1 synthetic pheromone blend was mixed in 4 mL lightweight paraffin oil in the 20 mL vials. All dispensers were suspended from the centre of a 2 L carton trap, hung at 1.5 m in an orchard block of "Red Delicious" apple trees in September 1988. Traps were set in a completely randomized design with each treatment having three replicates. Data were transformed to (n+±0.5) prior to ANOVA and Least Significant Difference test, P<0.05 (SAS Institute 1985).

Release rates for both coagulation and capillary tubes were determined in the laboratory at 25±1° C. by measurement of daily evaporation rate. Depletion of 5 μL of synthetic lure was monitored in seven tubes for each device and regression of the miniscus incorporated into the following equation:

$$\text{Release rate per day} = \frac{3.14 \times r^2 \times l \times d}{t}$$

where
r = radius of tube (cm)
l = length of miniscus regression (cm)
d = density of lure (0.856 g/mL)
t = observation time (days)

More male *C. verbasci* were trapped using synthetic lure at 1.0 and 2.0% concentration than at lower dosages (Table 2). We found that a concentration as low as 0.1% induced a significant response even under field conditions using a crude pheromone dispenser. Inexplicably, there was no significant response to live females in this experiment.

Attraction to the synthetic pheromone in two release devices equalled that of live females (Table 3). On the basis of these results, and those in Example 1, it is logical to conclude that there is a two-component pheromone in *C. verbasci*, comprising butyl butyrate and 2(E)-crotyl butyrate and that these components occur naturally in a ratio of 16:1. This is the first successful identification of a sex pheromone in the family Miridae.

TABLE 2

Mean number of male *C. verbasci* captured in dosage response experiment to butyl and crotyl butyrate (16:1) in 4 mL paraffin oil. Each treatment was replicated 3 times in a completely randomized design in an apple orchard, September 1988.

| Synthetic lure concentration | No. of males caught ($\bar{x}$ ± S.E.)[a] |
|---|---|
| 2.0% | 11.3 ± 2.3a |
| 1.0% | 8.7 ± 1.3a |
| 0.1% | 4.3 ± 1.8b |
| 0.01% | 2.0 ± 0.6bc |
| 5 live females | 1.0 ± 0.6c |
| Unbaited control | 0.0 ± 0.0c |

[a]Means followed by a common letter are not significantly different, P < 0.05, Least Significant Difference test (SAS Institute 1985).

EXAMPLE 3

The purpose of this example was to test the hypothesis that the catch of *C. verbasci* males in the autumn in response to female-produced sex pheromone could be used as a predictor of nymph density in apple orchards in the following spring, at the time that injury to fruitlets occurs. If this hypothesis proved true, the results might then be duplicated with the synthetic pheromone.

Female mullein bugs obtained from *V. thaosus* were used as a pheromone source, five being confined in a 140 mL plastic cup in which three 5 cm diameter holes were cut. Both the cup mouth and the holes were covered with fine mesh screening. A small portion of a flower stalk of mullein was inserted through the cup and held in a 11 mL vial of water. Females maintained on mullein remain attractive for about 7-10 days (Thistlewood 1986).

TABLE 3

Mean number of male *C. verbasci* captured in traps using three lure release devices containing μL of synthetic lure. Each treatment was replicated three times in a completely randomized design in an apple orchard, September 1988.

| Release device | Release rate (μg/day) | No. of males caught ($\bar{x}$ ± S.E.)[a] |
|---|---|---|
| Coagulation tube | 163 | 11.7 ± 1.5a |
| Capillary tube | 34 | 7.7 ± 1.9ab |
| 20 mL vial | 25 | 5.7 ± 1.8b |
| Unbaited control | — | 0.0 ± 0.0c |
| 5 live-caged females | — | 11.0 ± 2.9ab |

[a]Means followed by a common letter are not significantly different, P < 0.05, Least Significant Difference test, SAS Institute 1985.

A cage containing the females was pinned inside the top of a horizontal 2 L ice-cream carton trap (18.5×13 cm O.D.) lined with a cardboard insert covered with Sticky Stuff ™ (Olson Products Inc., Medina, Ohio). Two or three traps were deployed per orchard in the Okanagan Valley of British Columbia in 1987. Twenty-one such traps were in operation from Sep. 6–11, 1987, in seven orchards, and 27 were in Operation from Sep. 12 to Oct. 13, 1987 in ten orchards. Traps were hung 1.5 m above ground level, about 0.5 m inside the tree canopy. They were at least 8 m apart; none was placed in a border row. At least once a week from September 11 to Oct. 13, 1987, males were removed from the traps and all five females were replaced.

Five limbs on each trap-placement tree and one limb on each of four adjacent trees were tagged with plastic survey tape in the fall of 1987. To sample the nymph population in the spring of 1988, each tagged branch was tapped at 48 hour intervals beginning at "king bloom" and continuing until the mullein bug hatch was complete in each orchard. Simple regression analysis (SAS Institute 1985) was performed between the mean nymph density per limb (spring 1988) and the mean male bug capture per trap day (fall 1987) for each of five trapping intervals and for the entire period from Sep. 12 to Oct. 13, 1987 when 27 traps were in operation.

The captures of male *C. verbasci* in the fall ranged greatly (Table 4) suggesting that the traps were sensitive to different population levels. Movement of bugs to the orchards had begun prior to trap placement resulting in high numbers caught from the beginning of the experiment (Table 5). Captures remained high in the first week of October, but by October 13, they dropped to very low levels.

TABLE 4

*C. verbasci* capture rates in the Fall and nymph densities in Spring, in ten Okanagan Valley orchards. All means based on 17 replicates. Trap interval September 6 to October 13, 1987.

| Season | Criterion Assessed | Range | Mean ± S.E. |
|---|---|---|---|
| Fall | Total males trapped per tree | 3–120 | 35.9 ± 5.8 |
| | Males per trap per day | 0.1–4.1 | 1.1 ± 0.2 |
| Spring | Nymphs per trap tree limb | 0–11 | 2.4 ± 0.5 |
| | Nymphs per adjacent tree limb | 0.9 | 2.7 ± 0.6 |

Densities of nymphs per limb in the spring were also variable (Table 4). Mean numbers of nymphs per limb did not differ significantly (P>0.05) between trap and adjacent trees (Tukey's HSD Test, using a general linear model, SAS Institute 1985).

Figure 2:
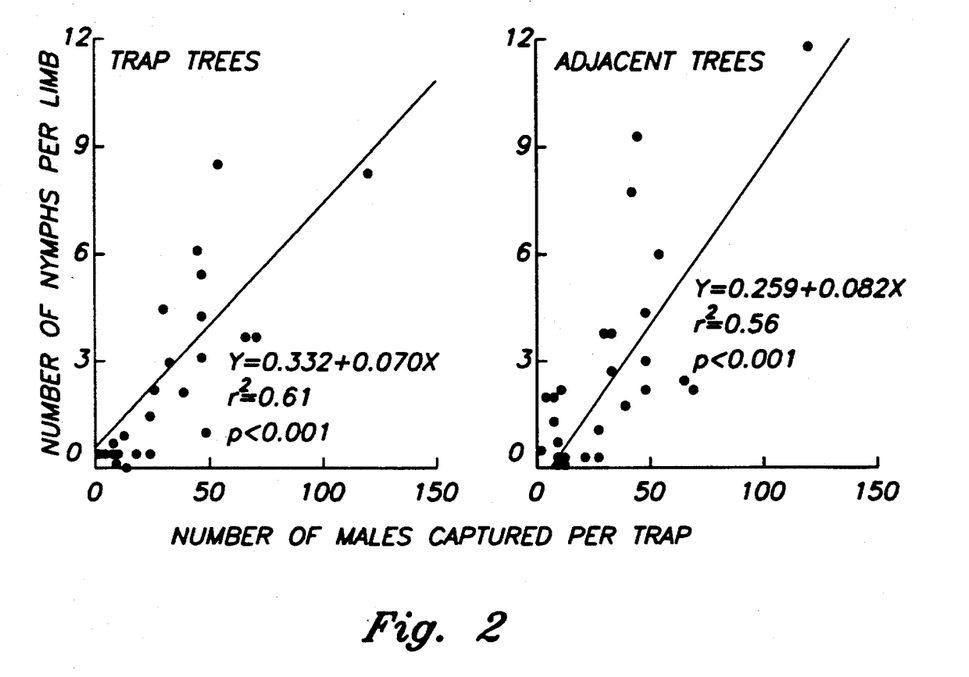
FIG. 2 depicts the relationship between catches of male *c. verbasci* in female-baited traps from 14 September to 13 October in the fall of 1987, and numbers of nymphs per limb the following spring.

We discovered there was a highly significant positive relationship between numbers of male *C. verbasci* trapped during most trap count intervals in the fall and density of nymphs in the spring in the trap trees (FIG. 2). A similar but slightly weaker relationship occurred for the trees adjacent to the ones in which the traps were placed. The relationships were also significant for the individual trapping intervals, with the exception of the final interval in October when the flight of adults had declined to a very low level (Table 5). These results with virgin females strongly suggested that a synthetic pheromone deployed in traps in the fall could also be used as a predictor of *C. verbasci* nymph densities in the following spring.

TABLE 5

Relationship between *C. verbasci* captures by trapping interval in the fall, 1987 and nymph densities in the spring, 1988 in ten Okanagan Valley orchards. P values based on regression analysis, General Linear Model (SAS Institute 1985).

| Trapping Interval | No. traps in operation | No. adults captured | Trap trees $r^2$ | p | Adjacent trees $r^2$ | p |
|---|---|---|---|---|---|---|
| 6-11 Sept. | 21 | 153 | 0.55 | 0.0001 | 0.50 | 0.0003 |
| 12-15 Sept. | 27 | 82 | 0.01 | 0.55 | 0.06 | 0.24 |
| 16-22 Sept. | 27 | 185 | 0.31 | 0.003 | 0.38 | 0.0006 |
| 23 Sept.-2 Oct. | 27 | 360 | 0.41 | 0.0003 | 0.45 | 0.0001 |
| 3-13 Oct. | 27 | 33 | 0.06 | 0.23 | 0.03 | 0.43 |

EXAMPLE 4

This example was conducted to determine whether a mixture of butyl butyrate with 2(E)-crotyl butyrate, the synthetic sex pheromone of *C. verbasci*, could be deployed in sticky traps in the fall as a predictor of nymph densities in the following spring.

In the fall of 1988, 75 wing traps with a sticky inside bottom (manufactured by Phero Tech Inc., Delta, British Columbia, Canada) were baited with a 16:1 mixture of butyl butyrate and 2(E)-crotyl butyrate. The pheromone was released at 34 µg/day from glass capillary tubes (1.0 mm I.D.) suspended inside the traps.

The traps were deployed in 2, 1 and 4 apple orchards located in the Okanagan Valley near Cawston, Summerland and Winfield, British Columbia, respectively. They were hung from branches of the trees 1.5 m above ground and about 0.5 m inside the canopy of the trees, and were in operation from Sep. 15-16 to Nov. 4, 1988.

In the spring of 1989, the orchards were surveyed for neonate nymphs using the standard limb tap method (Thistlewood and McMullen 1989). Due to growers' removal of some of the 1988 trees for replanting as well as early insecticide sprays that would have killed newly-hatched nymphs, 34 trap sites were eliminated from spring sampling.

Limb tap samples began May 11-12 at King bloom and were repeated on the same limbs 5 and 10 days thereafter, so as to sample all nymphs hatching from eggs on a given limb. Five limbs on each of the trap trees (trees in which traps had been hung) were sampled, as were one limb on each of the 6 or 8 trees surrounding 32 of the trap trees. Nine trap trees were eliminated from adjacent tree analysis because of variation in variety of adjacent trees, unusual horticultural practices (e.g. espaliered rows) or removal of surrounding trees. There were 6 or 8 adjacent trees depending on whether the rows were even or offset.

The numbers of nymphs per spring sample were transformed by $\log_{10}$. They were regressed against the catches of adult males in traps the previous fall. Due to very low catch rates in the first week and the last two weeks, these captures were deleted from the trap catch data prior to regression analysis, leaving a five-week fall sampling period. In addition, data from three very tall trees in the Summerland Orchard were deleted. These trees had relatively low capture rates in the fall, probably because most adult male *C. verbasci* were flying above the canopy (Bolvin et al. 1982), high above the traps. Conversely, there were very high nymph counts on these trees, probably because females, once mated, oviposited throughout the trees. All other trees were on dwarf root stock and the traps were much nearer the top of the canopy.

Figure 3:
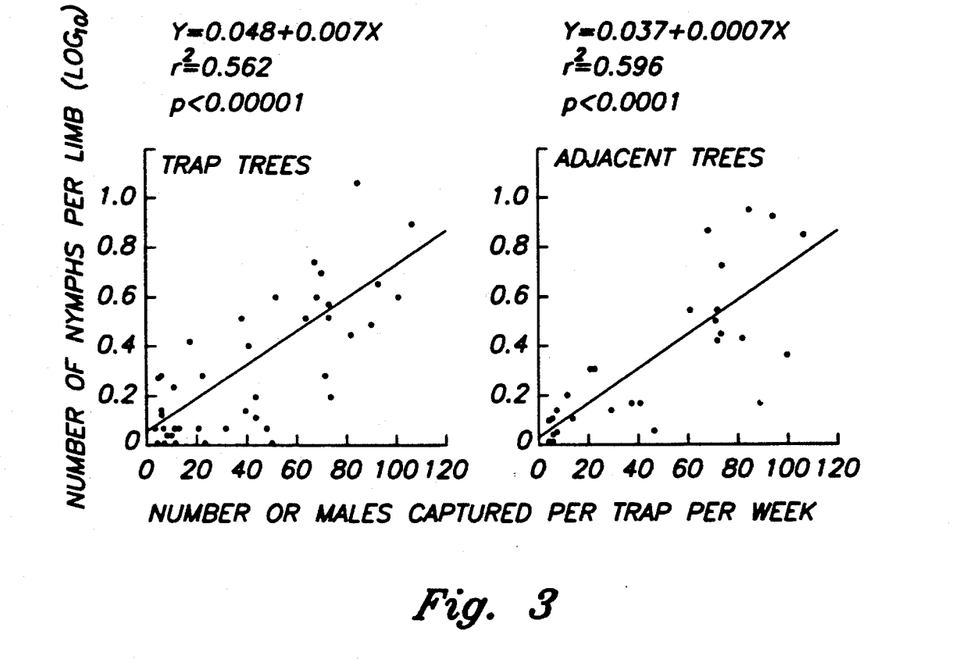
FIG. 3 depicts the relationship between catches of male *C. verbasci* in traps baited with synthetic sex pheromone from Sep. 22–23 to Oct. 20–21 1988, and numbers of nymphs per limb the following spring.
Figure 4:
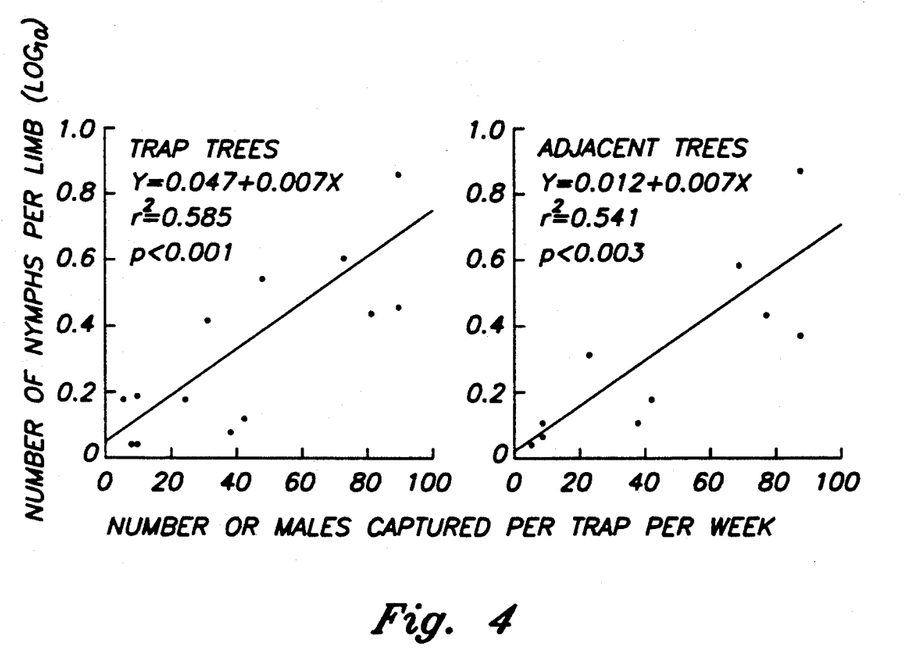
FIG. 4 depicts the relationship between catches of male *C. verbasci* grouped by orchard block in traps baited with synthetic sex pheromone from Sep. 20–23 to Oct. 20–21, 1988, and numbers of nymphs per limb grouped by orchard block the following spring.

We found that there were highly significant, positive relationships between *C. verbasci* nymph densities in the spring and catches of adult males in the fall, both for trap trees and adjacent trees (FIG. 3). Similar positive relationships persisted when the sample trees in a single block of trees in an orchard were grouped into three groups of four trees each, six groups of three trees each, and four groups of two trees each (FIG. 4).

These data indicate that the synthetic sex pheromones of *C. verbasci*, a mixture of butyl butyrate and 2(E)-crotyl butyrate can be used in the fall to predict nymph densities in the following spring.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

REFERENCES

Aldrich, J. R. 1988. Chemical ecology of the Heteroptera. A. Rev. Entomol. 33: 211-238.

Aldrich, J. R., W. R. Lusby, J. P. Kochansky, M. P. Hoffman, L. T. Wilson and F. G. Zalom. 1988. Lygus bug pheromones vis-a-vis stink bugs. pp. 213-215. In J. M. Brown (ed.) Beltwide Cotton Production Res. Conf., Proc., Nat. Cotton Counc. Am., Memphis, Tenn.

Boivin, G. and R. K. Stewart. 1982. Attraction of male green apple bugs, *Lygocoris communis* (Hemiptera: Miridae) to caged females. Can. Entomol. 114: 765-766.

Boivin, G., R. K. Stewart and I. Rivard. 1982. Sticky traps for monitoring phytophagous mirids (Hemiptera: Miridae) in an apple orchard in southwestern Quebec. Environ. Entomol. 11: 1067-1070.

Hardman, J. M., R. E. L. Rogers and C. R. Maclellan. 1984. Pest abundance, pesticide usage and levels of fruit damage in a pest management program in Nova Scotia apple orchards. XVII Intl. Congr. Entomol., Hamburg, W. Germany 1985.

Madsen, H. F. 1981. Monitoring codling moth populations in British Columbia apple orchards, pp. 57-62. In Mitchell, E.M. (ed.). Management of insect pests with semiochemicals. Concepts and practice. Plenum Process, New York.

McMullen, R. D. and C. Jong. 1970. The biology and influence of pesticides on *Campylomma verbasci* (Heteroptera: Miridae). Can. Entomol. 102:1390-1394.

Pierce, H. D., A. M. Pierce, J. G. Millar, J. W. Wong, V. G. Verigin, A. C. Oehlschlager and J. H. Borden. 1984. Methodology for isolation and analysis of aggregation pheromones in the genera Cryptolestes and Oryzaephilus (Coleoptera: Cucujidae). pp. 121–137. In Proc. 3rd Intern. Wkg. Conf. on Stored Products Entomol., Manhattan, Kans.

Sas Institute. 1985. SAS User's guide: statistics, 5th ed. Sas Institute, Cary, N.C.

Scales, A. L. 1968. Female tarnished plant bugs attract males. J. Econ. Entomol. 61:1466–1467.

Smith, E. S. C. 1977. Presence of sex attractant pheromone in *Helpceltis clavifer* (Walker) (Heteroptera: Miridae). J. Aust. Entomol. Soc. 16: 113–116.

Staddon, B. W. 1986. The scent glands of Heteroptera. Adv. Insect. Physiol. 14:351–418.

Thistlewood, H. M. A. 1986. The bionomics and monitoring of *Campylomma verbasci* (Meyer) on apple in the Okanagan Valley, British Columbia. PhD. thesis. Dept. of Biological Sciences, S.F.U.

Thistlewood, H. M. A. and R. D. McMullen. 1989. Distribution of *Campylomma verbasci* (Meyer) (Heteroptera: Miridae) nymphs on apple and an assessment of two methods of sampling. J. Econ. Entomol. 82: 510–515.

Thistlewood, H. M. A., D. McMullen, and J. H. Borden. 1989a. Damage and economic injury levels of the mullein bug *Campylomma verbasci* (Meyer) (Heteroptera: Miridae), on apple in the Okanagan Valley. Can. Entomol. 121:1–9.

Thistlewood, H. M. A., J. H. Borden, R. F. Smith, H. D. Pierce, Jr., and R. D. McMullen. 1989b. Evidence for a sex pheromone in the mullein bug *Campylomma verbasci* (Meyer) (Heteroptera: Miridae). Can. Entomol. 121: 737–744.

Washington State University. Cooperative Extension. 1988. Spray guide for tree fruit in Eastern Washington. Publication EBO419.

Whalon, M. E. and B. A. Croft. 1984. Apple I.P.M. implementation in North America. A. Rev. Entomol. 29: 435–470.

What is claimed is:

1. A composition for attracting male mullein bugs, *Campylomma verbasci* comprising a mixture of an effective amount of butyl butyrate and an effective amount of 2 (E)-crotyl butyrate.

2. A method of attracting and capturing *Campylomma verbasci* comprising baiting traps with a mixture of an effective amount and release rate of butyl butyrate and an effective amount and release rate of 2 (E) crotyl butyrate to provide a *Campylomma verbasci* attractive mixture.

3. A method of predicting densities of *Campylomma verbasci* nymphs in the spring which comprises correlating the densities in the spring to the numbers of male *Campylomma verbasci* captured in the previous fall in traps baited with an effective number of female *Campylomma verbasci*.

4. A method of predicting densities of *Camplylomma verbasci* nymphs in the spring which comprises extrapolating the densities in the spring from the numbers of male *Campylomma verbasci* captured in the previous fall in traps baited with a mixture of an effective amount of butyl butyrate and an effective amount of 2 (E)-crotyl butyrate.

5. A composition as claimed in claim 1 wherein the butyl butyrate and 2(E)-crotyl butyrate are synthetic.

6. A composition as claimed in claim 1 or 5 wherein the ratio by weight of butyl butyrate to 2(E)-crotyl butyrate is 16 to 1.

* * * * *